(12) United States Patent
Byrne et al.

(10) Patent No.: US 12,702,574 B2
(45) Date of Patent: Aug. 11, 2026

(54) SLEEVE PULL BACK MECHANISM

(71) Applicant: W. L. Gore & Associates, Inc., Newark, DE (US)

(72) Inventors: Austin A. Byrne, Flagstaff, AZ (US); Rebecca L. Maryn, Flagstaff, AZ (US); Jilene M. Oakley, Flagstaff, AZ (US); Michael J. Shepard, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 561 days.

(21) Appl. No.: 18/269,856

(22) PCT Filed: Dec. 28, 2020

(86) PCT No.: PCT/US2020/067156
§ 371 (c)(1),
(2) Date: Jun. 27, 2023

(87) PCT Pub. No.: WO2022/146411
PCT Pub. Date: Jul. 7, 2022

(65) Prior Publication Data

US 2024/0058146 A1 Feb. 22, 2024

(51) Int. Cl.
*A61F 2/97* (2013.01)
*A61M 25/06* (2006.01)

(52) U.S. Cl.
CPC ........... *A61F 2/97* (2013.01); *A61M 25/0668* (2013.01)

(58) Field of Classification Search
CPC .. A61F 2/97; A61F 2/962; A61F 2/966; A61F 2/9662; A61F 2002/9511
See application file for complete search history.

(56) References Cited

U.S. PATENT DOCUMENTS

| | | | |
|---|---|---|---|
| 6,733,520 | B2 | 5/2004 | Yang et al. |
| 9,375,308 | B2 | 6/2016 | Norris |
| 9,402,755 | B2 | 8/2016 | Norris et al. |
| 9,610,183 | B2 | 4/2017 | Norris et al. |
| 10,213,329 | B2 | 2/2019 | Cully et al. |
| 2002/0038140 | A1 | 3/2002 | Yang et al. |

(Continued)

FOREIGN PATENT DOCUMENTS

| | | |
|---|---|---|
| CN | 109688984 A | 4/2019 |
| CN | 111671552 A | 9/2020 |

(Continued)

OTHER PUBLICATIONS

International Preliminary Report on Patentability received for PCT Patent Application No. PCT/US2020/067156, mailed on Jul. 13, 2023, 10 pages.

(Continued)

*Primary Examiner* — Bruce E Snow

(57) ABSTRACT

Through observation it has been determined that deployment of delivery sleeves may result in one or more portions of the deliver), sleeve extending beyond an end of the endoluminal device resulting in an overhang of material. The overhang may affect blood flow through the endoprosthesis or otherwise impact performance, including facilitating unwanted tissue growth. Various inventive concepts are provided for addressing (reducing or removing) constraining sheath overhang.

20 Claims, 13 Drawing Sheets

(56) References Cited

U.S. PATENT DOCUMENTS

| | | | | |
|---|---|---|---|---|
| 2002/0151956 | A1 | 10/2002 | Chobotov et al. | |
| 2003/0004561 | A1 | 1/2003 | Bigus et al. | |
| 2006/0015171 | A1 | 1/2006 | Armstrong | |
| 2010/0145430 | A1 | 6/2010 | Wuebbeling et al. | |
| 2012/0065644 | A1 | 3/2012 | Ng et al. | |
| 2012/0130475 | A1 | 5/2012 | Shaw | |
| 2013/0018450 | A1 | 1/2013 | Hunt | |
| 2013/0123896 | A1 | 5/2013 | Bloss et al. | |
| 2013/0158647 | A1 | 6/2013 | Norris et al. | |
| 2013/0245743 | A1 | 9/2013 | Norris | |
| 2014/0046430 | A1* | 2/2014 | Shaw | A61F 2/97 623/1.12 |
| 2014/0135894 | A1* | 5/2014 | Norris | A61F 2/966 623/1.12 |
| 2023/0255761 | A1 | 8/2023 | Chang et al. | |
| 2024/0058146 | A1* | 2/2024 | Byrne | A61F 2/97 |

FOREIGN PATENT DOCUMENTS

| | | | |
|---|---|---|---|
| JP | 2008-506459 | A | 3/2008 |
| JP | 2014-501563 | A | 1/2014 |
| JP | 2015-509814 | A | 4/2015 |
| JP | 2015-513926 | A | 5/2015 |
| WO | 2006/019626 | A2 | 2/2006 |
| WO | 2012/068046 | A2 | 5/2012 |
| WO | 2013/137977 | A1 | 9/2013 |
| WO | 2013/137978 | A1 | 9/2013 |
| WO | 2018/165358 | A1 | 9/2018 |

OTHER PUBLICATIONS

International Search Report and Written Opinion received for PCT Patent Application No. PCT/US2020/067156, mailed on Sep. 30, 2021, 14 pages.

* cited by examiner

SLEEVE PULL BACK MECHANISM

CROSS-REFERENCE TO RELATED APPLICATION

This application is a national phase application of PCT Application No. PCT/US2020/067156, internationally filed on Dec. 28, 2020, which is herein incorporated by reference in its entirety for all purposes.

FIELD

The present disclosure relates generally to medical device deployment systems or other delivery systems, including endoluminal devices with delivery sleeves, and more specifically to medical device deployment systems configured to reduce delivery sleeve overhang upon deployment of an endoluminal device.

BACKGROUND

Endoluminal devices are frequently used to treat the vasculature of human patients. It is generally known to utilize a flexible sleeve for constraining the device toward an outer peripheral dimension or delivery configuration suitable for endoluminal delivery toward a vascular treatment site. It may be desirable to at least partially retract such a sleeve, for example, a sleeve configured to remain in situ after deployment of the underlying endoluminal device, for example, so as to prevent inadvertent obstruction of a branch vessel by the sleeve. Clinicians may not be able to rely exclusively on conventional imaging technologies to avoid such inadvertent obstruction because, inter alia, (i) such imaging technologies may not detect sleeves themselves, (ii) sleeves may not comprise radiopaque markers, and (iii) radiopaque bands or other markers on endoluminal devices may not necessarily correlate to the ends of sleeves.

U.S. Pat. No. 10,219,929, entitled "Sleeve Retraction System," and issued Mar. 5, 2019 describes systems for endoluminal devices utilizing a sleeve for constraining an expandable device toward a constrained configuration suitable for endoluminal delivery to a treatment site along vasculature and a mechanism for retracting at least a portion of the sleeve.

SUMMARY

Through observation it has been determined that deployment of delivery sleeves may result in one or more portions of the delivery sleeve extending beyond an end of the endoluminal device resulting in an overhang of material. The overhang may affect blood flow through the endoprosthesis or otherwise impact performance, including facilitating unwanted tissue growth. Various inventive concepts are provided for addressing (reducing or removing) constraining sheath overhang.

According to an example ("Example 1") of the present disclosure, a delivery system is disclosed. The delivery system comprises a delivery sleeve releasably secured in a tubular shape configured to constrain a medical device in a delivery configuration. The delivery sleeve has a length, an upstream edge, a down stream edge, a m id-region between the upstream edge and the downstream edge, a first margin extending along the length of the delivery sleeve, a second margin extending a long the length of the delivery sleeve, and a first corner region proximate the upstream edge. The delivery system also comprises a first deployment line section releasably coupling the first and second margins of the delivery sleeve such that the delivery sleeve is releasably secured in a tubular shape and a second deployment line section anchored to the first corner region and routed from the first corner region to a first anchor point at the mid-region. The second deployment line section is configured so that upon actuation of the second deployment line section, at last a portion of the upstream edge is translated toward the mid-region.

Referring to Example 1, the second deployment line section may extend form the first deployment line section. The delivery sleeve may have a second corner region proximate the upstream edge and the second deployment line section may be anchored to the second corner region and routed to the first anchor point at the mid-region, wherein the second deployment line section is configured so that upon actuation of the second deployment line section, both of the corner regions are translated toward the mid-region. The second deployment line section may be routed outside of the delivery sleeve.

Still referring to Example 1, the first corner region may include an aperture through which the second deployment line section is routed to anchor the second deployment line section to the first corner region. The deployment system may include an auxiliary sleeve. Where the deployment system includes an auxiliary sleeve, the auxiliary sleeve may be positioned around the medical device and the delivery sleeve.

According to another example ("Example 2") of the present disclosure, a delivery system is disclosed. The delivery system comprises a delivery sleeve configured to constrain a medical device in a delivery configuration. The delivery sleeve has a length, an upstream edge, a downstream edge, a mid-region, and a first corner region. The delivery system further comprises a first deployment line section extending along the length of the delivery sleeve from the downstream edge to the upstream edge to releasably couple the delivery sleeve in a tubular configuration and a second deployment line section coupled from the first deployment line section. The second deployment line section is coupled to the first corner region and routed from the first corner region to the mid-region and anchored at the mid-region at a first anchor point.

Referring to Example 2, the second deployment line section may be configured so that upon actuation of the second deployment line section, the first corner region is translated back toward the mid-region. The first deployment line section and the second deployment line section may be releasable from the delivery sleeve.

Still referring to Example 2, the delivery sleeve may have a second corner region. In such an example the second deployment line section may be coupled to the second corner region and routed from the second corner region to the mid-region and anchored at the first anchor point, wherein the second deployment line section is configured so that upon actuation of the second deployment line section, the first corner region and the second corner region are translated back toward the m id-region.

According to yet another example ("Example 3") of the present disclosure, a method for actuating a delivery sleeve of a delivery system is disclosed. The method comprises positioning the delivery sleeve at a desired location. The delivery sleeve forms part of a delivery system, which includes a medical device with which the delivery sleeve is associated, wherein the delivery sleeve has an upstream edge, a downstream edge, a mid-region, and at least one corner. The delivery system further includes a first deployment line attached to the delivery sleeve and a second deployment line section attached to the at least one corner and routed through the mid-region. The method further comprises applying tension to the first deployment line section such that the first deployment line section actuates the delivery sleeve to effectuate delivery of the medical device and applying tension to the second deployment line section such that the second deployment line section translates the at least one corner back toward the m id-region.

Referring to Example 3, the first and second deployment line sections may be portions of a single deployment line. The method may further comprise the step of applying tension to the second deployment line section so that the first deployment line section and the second deployment line section are released from the delivery sleeve.

According to another example ("Example 4") of the present disclosure, a method for delivering a medical device is disclosed. The method comprises positioning a delivery system at a desired location in a body of a patient. The delivery system includes a delivery sleeve associated with a medical device. The delivery sleeve has an upstream edge, a downstream edge, a mid-region, and at least one corner. The delivery system further comprises an auxiliary sleeve positioned around the medical device and the delivery sleeve, wherein the auxiliary sleeve has an upstream edge. The delivery system further comprises a deployment line including a first deployment line section coupled to the first delivery sleeve and a second deployment line section coupled to the auxiliary sleeve, wherein the deployment line is attached to the at least one corner of the delivery sleeve and routed through the mid-region of the delivery sleeve.

The method of Example 4 further comprises releasing the auxiliary sleeve from about the medical device and the delivery sleeve; applying tension to the first deployment line section to release the delivery sleeve; and applying tension to the second deployment line section to translate the upstream edges of each of the first delivery sleeve and the second delivery sleeve toward the mid-region of the first delivery sleeve.

Still referring to Example 4, the delivery system may be coupled to a catheter. In such an example, the method may further comprise applying tension to the second deployment line section so that the first deployment line section and the second deployment line section are released form the delivery sleeve and the auxiliary sleeve into the catheter.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
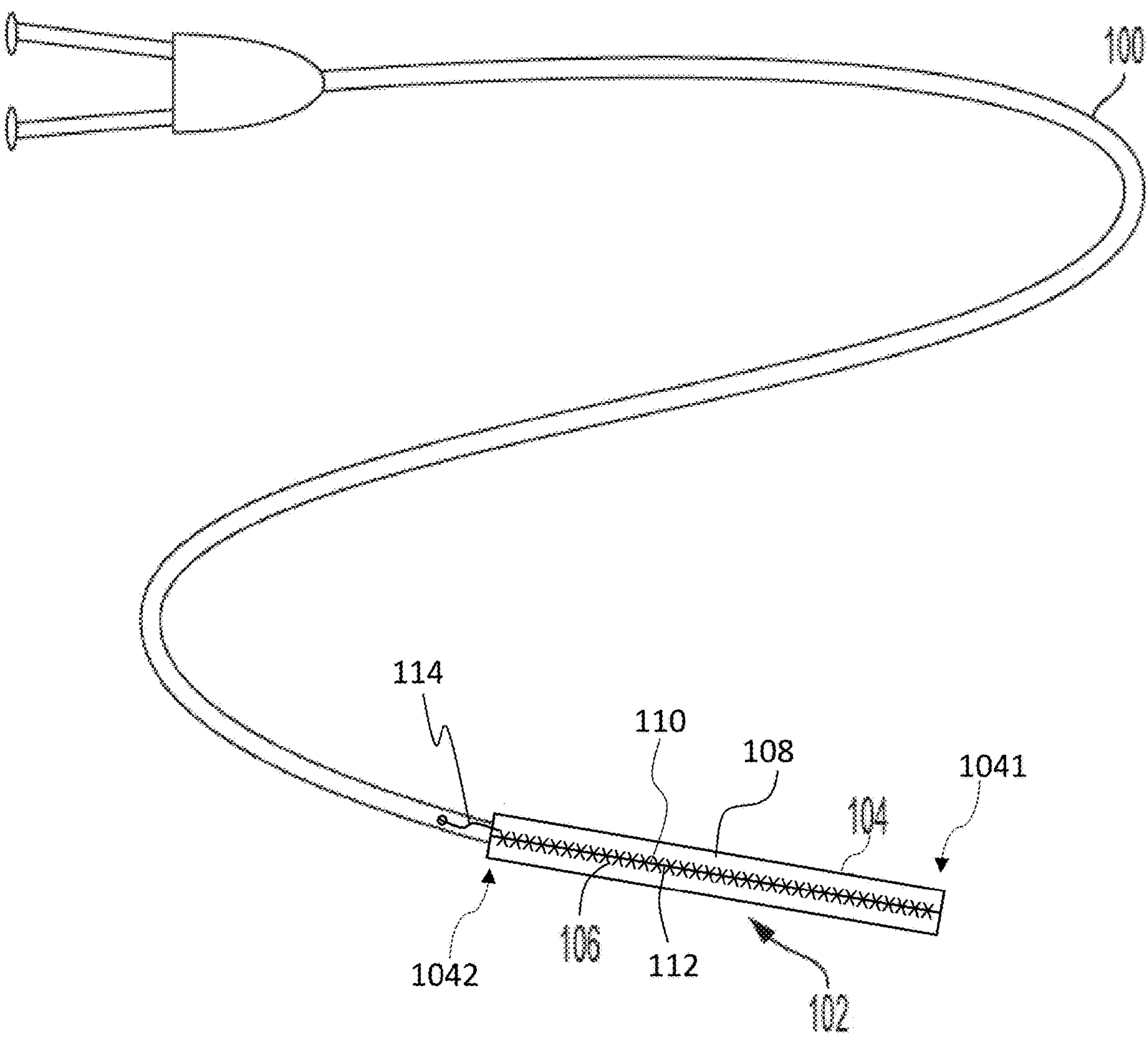
FIG. 1 shows a catheter including at least one sleeve configured to constrain a medical device, according to some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale but may be exaggerated to illustrate various aspects of the present disclosure, and in that regard, the drawing figures should not be construed as limiting.

Definitions and Terminology

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

Endoluminal devices are frequently used to treat the vasculature of human patients. These treatments or procedures are commonly referred to as intraluminal or endovascular procedures. Such devices often include a sleeve. As used herein, the term "sleeve" refers to a primary, secondary, tertiary, etc., sleeve, sheath, or the like, that constrains an endoluminal device toward a collapsed configuration or outer peripheral dimension suitable for endoluminal delivery of the device to a treatment portion of the vasculature of a patient.

For purposes of the disclosure, the term "constrain" may mean (i) to limit the expansion, either through self-expansion or assistance by a device (e.g., a balloon), of the diameter of at least a portion of a medical device or (ii) to cover or surround but not otherwise restrain at least a portion of a medical device (e.g., for storage or biocompatibility reasons and/or to provide protection to the medical device and/or the vasculature). For reference, the term "diameter" is not meant to require a circular cross-section and is instead to be understood broadly to reference a maximum transverse cross-sectional dimension of the medical device.

As used herein, the term "endoluminal device" or "device" refers to stents, grafts, filters, valves, anchors, occluders, and other implantable devices, and also includes all of the foregoing constrained in one or more sleeves.

As used herein, the term "line" refers to any type of string, cord, thread, fiber, or wire, and can be comprised of metallic, polymeric, or natural materials, including conventional medical grade materials such as nylon, polyacrylamide, polycarbonate, polyethylene, polyform aldehyde, polymethylmethacrylate, polypropylene, polytetrafluoroethylene, expanded polytetrafluoroethylene, polytrifluorochlorethylene, polyvinylchloride, polyurethane, elastomeric organosilicon polymers; metals such as stainless steels, cobalt-chromium alloys and nitinol; and high strength polymer fibers such as ultra-high molecular weight polyethylene fibers or aramid fibers.

Throughout this specification and the claims, the terms "distal" or "leading" may refer to a relative location on a device which is closer to the end of the device that is inserted into and progressed through the vasculature of a patient. The terms "proximal" or "trailing" may refer to a relative location on a device which is closer to the end of the device that is located outside of the vasculature of a patient. In related terms, the terminology "distal end" can be interpreted as a "far end" and "proximal end" and a "near end."

This disclosure is not meant to be read in a restrictive manner. For example, the terminology used in the application should be read broadly in the context of the meaning those in the field would attribute such terminology.

DESCRIPTIONS OF THE DISCLOSED EMBODIMENTS

Medical devices may include different stages of deployment for implantation in a body of a patient. For example, a medical device may include an undeployed, delivery configuration in which at least a portion of the medical device is contained in at least one constraint or sleeve that constrains the device for delivery into the vasculature of a patient. When the device has been delivered into the vasculature of a patient, the constraint is removed, allowing the device to be deployed and expanded in a manner complementary to the vasculature. For reference, the term "removed" as used with respect to the delivery sleeve is synonymous with "released," and does not require physical removal from the body.

The delivery sleeve may be comprised of, for example, expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Other instances for the sleeve material may include high strength polymer fibers such as ultra-high molecular weight polyethylene fibers or aramid fibers. The sleeve may include a bioactive agent. Any sleeve which may be used to constrain an endoluminal device is in accordance with the present disclosure.

For example, referring to FIG. 1, a delivery system including a catheter 100 with a sleeve 102 is shown according to some embodiments. As shown in FIG. 1, the sleeve 102 may be a primary sleeve, such as delivery sleeve 116, or a secondary sleeve, such as auxiliary sleeve 118, as discussed further herein. The sleeve 102 is configured to cover a medical device 104 and/or constrain the medical device 104 to a delivery configuration. The sleeve 102 includes a body 108 that is maintained in a tubular shape, where the body 108 includes opposing edges 110, 112 releasably secured together with at least one fiber, or deployment line 106. The body 108 may be formed of a sheet or layer of material that is wrapped into a tubular form (e.g., cigarette wrapped). For example, the opposing edge 110 and the opposing edge 112 may be defined by a first margin 110 extending along the length of the sleeve 102 and a second margin 112 extending along the length of the sleeve 102. The sleeve 102 is configured to be arranged about the medical device 104 and may cover and/or maintain the medical device 104 in the delivery configuration. At a desired time the sleeve 102 is able to be released by releasing the opposing edges 110, 112 of the sleeve using the deployment line 106. The sleeve 102 is optionally secured to the medical device 104 such that the sleeve 102 remains in the body following release; otherwise, the sleeve 102 or a portion of the sleeve 102 may be removed. For example, a portion of the body 108 of the sleeve 102 may be secured to the medical device 104 (e.g., using a suture or fiber) such the sleeve 102 stays in the patient's body with the medical device 104.

As shown, the sleeve 102 is arranged along a length of the medical device 104 and circumferentially around the medical device 104, so that at least a portion of (e.g., some or all of the length of) the medical device 104 is covered and/or constrained for delivery. The deployment line 106 may be arranged within a lumen (not shown) of the catheter 100 and extend toward a proximal end of the catheter 100 that is arranged external to a patient during delivery of the medical device 104. The deployment line 106 includes a proximally-extending portion 114, or end 114 that a user may apply tension to in order to release the sleeve 102 and deploy the medical device 104. The medical device 104 may be a stent, stent-graft, a balloon, filter, heart valve, or a similar device as desired.

Although other configurations of the sleeve 102 can be used, a preferred configuration is a generally rectangular one having constant width, although tapered or stepped configurations, for example, are contemplated. The sleeve 102 may be described as having side margins that extend between the ends of the sleeve 102. Eyelets, also described as openings or apertures, are optionally disposed along the side margins so that a coupling member, such as the deployment line 106, may be laced or threaded therethrough. The eyelets may be in the form of through holes, which may be formed by a uniform-diameter puncturing device or by other means such as laser-drilling. Alternatively, the eyelets may be formed by loops of material (e.g., fibers) which may be attached to the side margins or formed by other means.

The device 104 includes a delivery diameter and a deployed diameter that is larger than the delivery diameter. The removable sleeve 102 is attached to the device 104 at its delivery diameter. As mentioned above, the removable sleeve illustratively includes a deployment line 106 configured to release the sleeve 102 and transition the medical device 104 from the delivery diameter to the deployed diameter in response to a force applied to the deployment line 106. The device 104 further includes an upstream, proximal edge 1041 and a downstream, distal edge 1042 corresponding to upstream and downstream edges of the removable sleeve 102, further discussed herein.

The medical device 104 may have any of a variety of desired deployed diameters (e.g., from about 5 mm to about 15 mm, about 6 mm to about 9 mm, about 6 mm to about 12 mm, about 10 mm to about 20 mm, about 15 mm to about 30 mm, or about 25 mm to about 45 mm), and any desired delivery diameter that is less than the deployed diameter. For example, in some instances, a ratio of the delivery diameter of the medical device 104 to the deployed diameter of the device 104 is less than about 0.3, less than about 0.29, less than about 0.28, less than about 0.27, or less than about 0.26, for example. For reference, the term "diameter" is not meant to require a circular cross-section and is instead to be understood broadly to reference a maximum transverse cross-sectional dimension of the medical device 104.

Figure 2A:
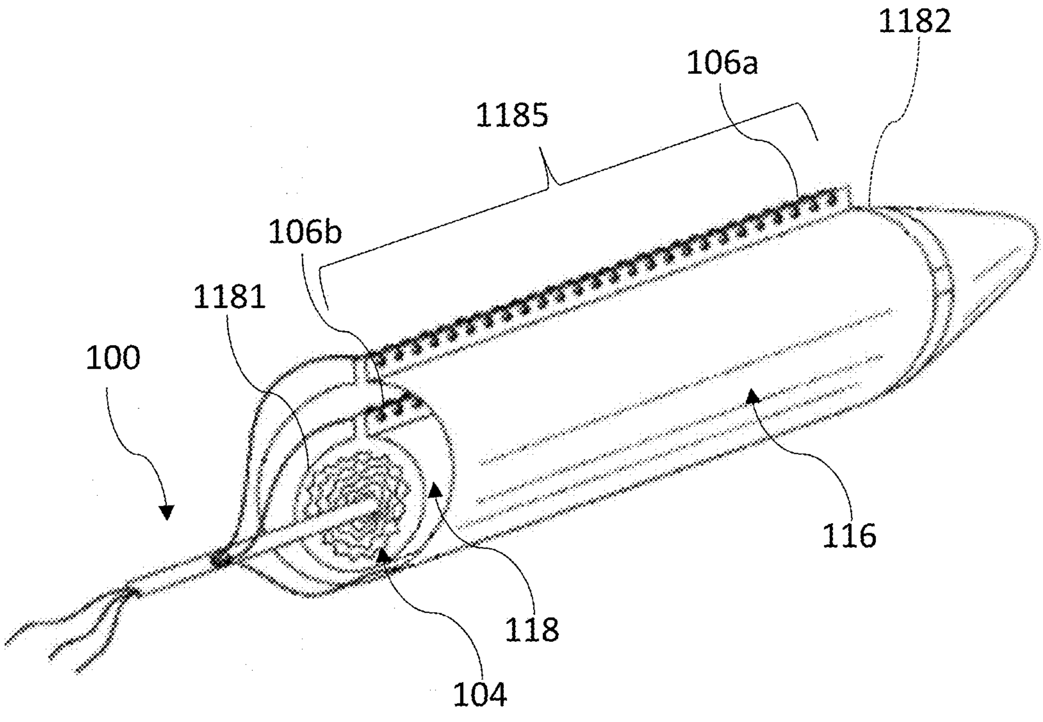
FIG. 2A shows a catheter including at least two sleeves configured to constrain a medical device, according to some embodiments.

Referring now to FIG. 2A, in some embodiments, the medical device 104 includes both a primary sleeve, or delivery sleeve 116, and a secondary sleeve, or auxiliary sleeve 118. Utilization of multiple, overlapping (either partially of fully overlapping) sleeves (i.e., more than two) may allow the device to be deployable between multiple (i.e., more than two) diameters. For example, the medical device 104 may be deployable from a delivery diameter, to an intermediate deployment diameter, and then to a final deployment diameter.

In some instances, the auxiliary sleeve 118 is configured to constrain the device 104 at an intermediate diameter during delivery, while the delivery sleeve 116 is configured to be positioned about the auxiliary sleeve 118 to constrain the device to the delivery diameter prior to delivery. In such an embodiment, the delivery sleeve 116 must be deployed at the same time as or before the auxiliary sleeve 118 may be deployed. The delivery sleeve 116 may include a first deployment line section **106*a*, which allows a user to deploy the delivery sleeve 116. For example, actuation of the first deployment line section 106*a*** results in release of the device from the delivery diameter to an intermediate diameter of the device.

Still referring to FIG. 2A, the auxiliary sleeve 118 includes an upstream, proximal edge 1181, a downstream, distal edge 1182, and a mid-region 1185 positioned between the proximal edge 1181 and the distal edge 1182. A second deployment line section **106*b* of the auxiliary sleeve 118 allows a user to deploy the auxiliary sleeve 118. For example, actuation of the second deployment line section 106*b* results in release of the device 104 to an expanded diameter greater than the intermediate diameter. In some embodiments, the deployment line sections 106*a*, 106*b* comprise at least two separate lines, which are actuated independently in order to effect deployment of the respective delivery sleeve 116 and auxiliary sleeve 118. In other embodiments, the deployment line sections 106*a* and 106*b* comprise a single deployment line 106, which may be actuated to deploy the delivery sleeve 116, and then further actuated to deploy the auxiliary sleeve 118. In either embodiment, the auxiliary sleeve 118 may be deployed immediately upon deployment of the delivery sleeve 116, or a time after deployment of the delivery sleeve 116. For example, after deployment of the delivery sleeve 116, a user may immediately deploy the auxiliary sleeve 118. Otherwise, a discretionary period of time may pass between the deployment of the delivery sleeve 116 and deployment of the auxiliary sleeve 118**.

Figure 2B:
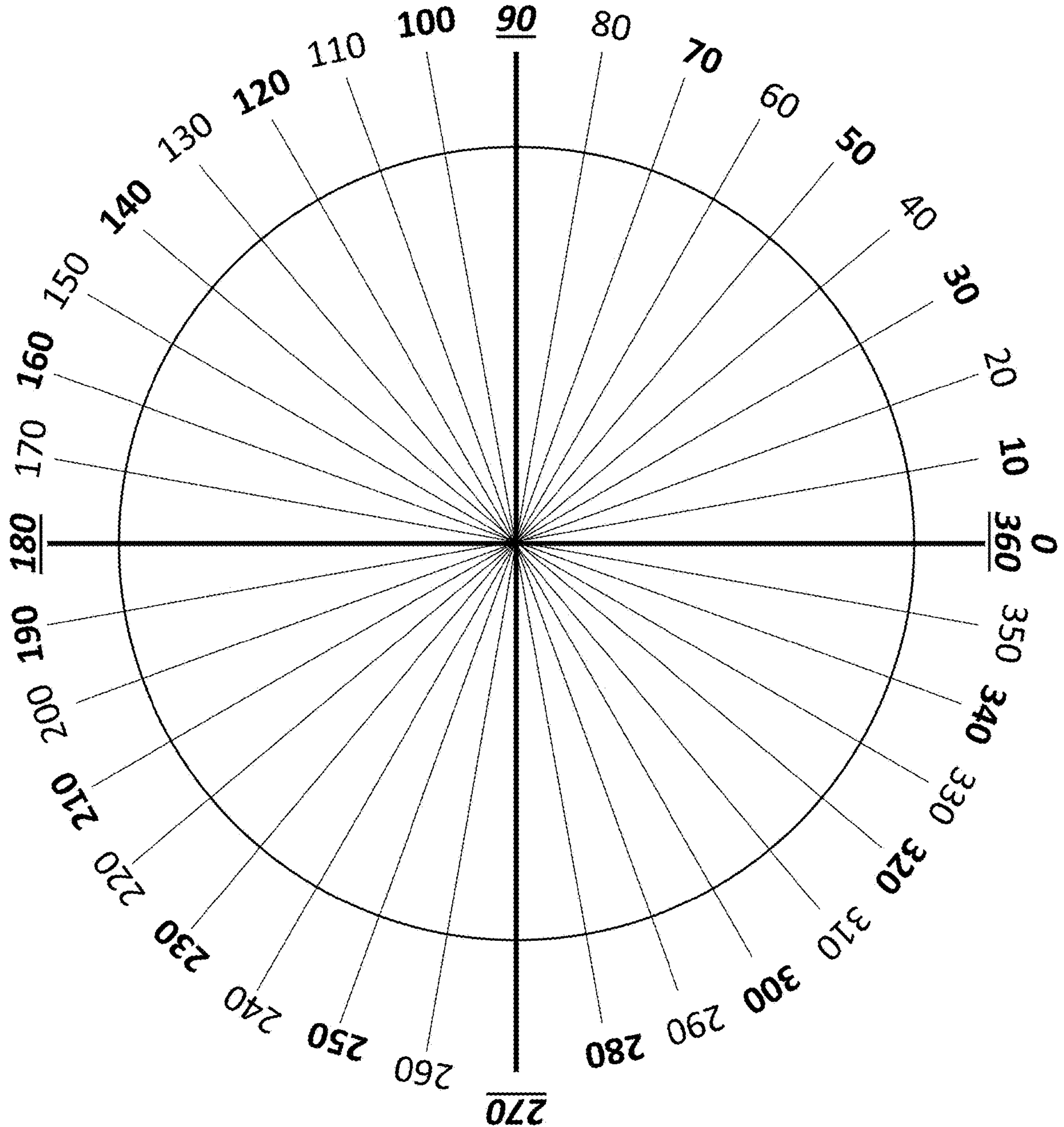
FIG. 2B shows the degree designations of a cylindrical device.

Referring briefly to FIG. 2B, it is noted that a sleeve 1118 (FIG. 3A) generally covers a cylindrical device 104 (FIG. 1), so that one edge of the sleeve between the proximal edge 1181 (FIG. 2A) and the distal edge 1182 (FIG. 2A) is designated at 0° region of a circumference of the cylindrical device and another edge of the sleeve between the proximal edge 1181 (FIG. 2A) and the distal edge 1182 (FIG. 2A) is designated at 360° region of the circumference. A key "K1" is provided with each of the plan views of the sleeve discussed further herein to illustrate the degree region of the sleeve through which the deployment line 106 (FIG. 1) is routed as described above.

Furthermore, the deployment line 106 (FIG. 1) may be routed at different angles from one anchor point to another. Such angles are referred to herein and are different from the degree region designations 0°-360° of the circumference of the cylindrical device. A key "K2" is provided with each of the plan views of the sleeve discussed further herein to illustrate the angles at which the deployment line is routed, the degrees of each angle being designated with an "A".

The proximal edge 1181 includes notations 1P, 2P, 3P, 4P, 5P, 6P, 7P, 8P, and 9P to correspond with proximal stent apices. For example, as described herein, a stent apex may include a 1PX notation, wherein the "1P" designates the column of apices on the proximal edge 1181 of the sleeve 1118 as labeled and the "X" designates the number of rows distal from the proximal edge 1181 in which the corresponding stent apex may be found. Similarly, the distal edge 1182 includes notations 1D, 2D, 3D, 4D, 5D, 6D, 7D, 8D, and 9D to correspond with distal stent apices. For example, as described herein, a stent apex may include a 1DX notation, wherein the "1D" designates the column of apices on the distal edge 1182 of the sleeve 1118 as labeled and the "X" designates the number of rows proximal from the distal edge 1182 in which the corresponding stent apex may be found.

The notations of each stent apices may further be interchangeably referred to as "anchor points," wherein each anchor point, or stent apex, may or may not be used to anchor the deployment line as further described herein. "Stent apex" or "stent apices" may be used interchangeably with "anchor point" or "anchor points" or may further be used interchangeably with "reference point" or "reference points" wherein each reference point refers to a point on the device 104 corresponding with an anchor point and/or stent apex closest to the given notation. Notably, such reference points only correspond to the device 104 being shown. The routing pattern provided herein may be applied to a varying number of devices having different sizes. In other words, the routing pattern may be scaled to apply to any device, wherein the notations referenced herein refer to the reference point, anchor point, or stent apex located the most closely to the notation after scaling of the pattern.

Figure 3A:
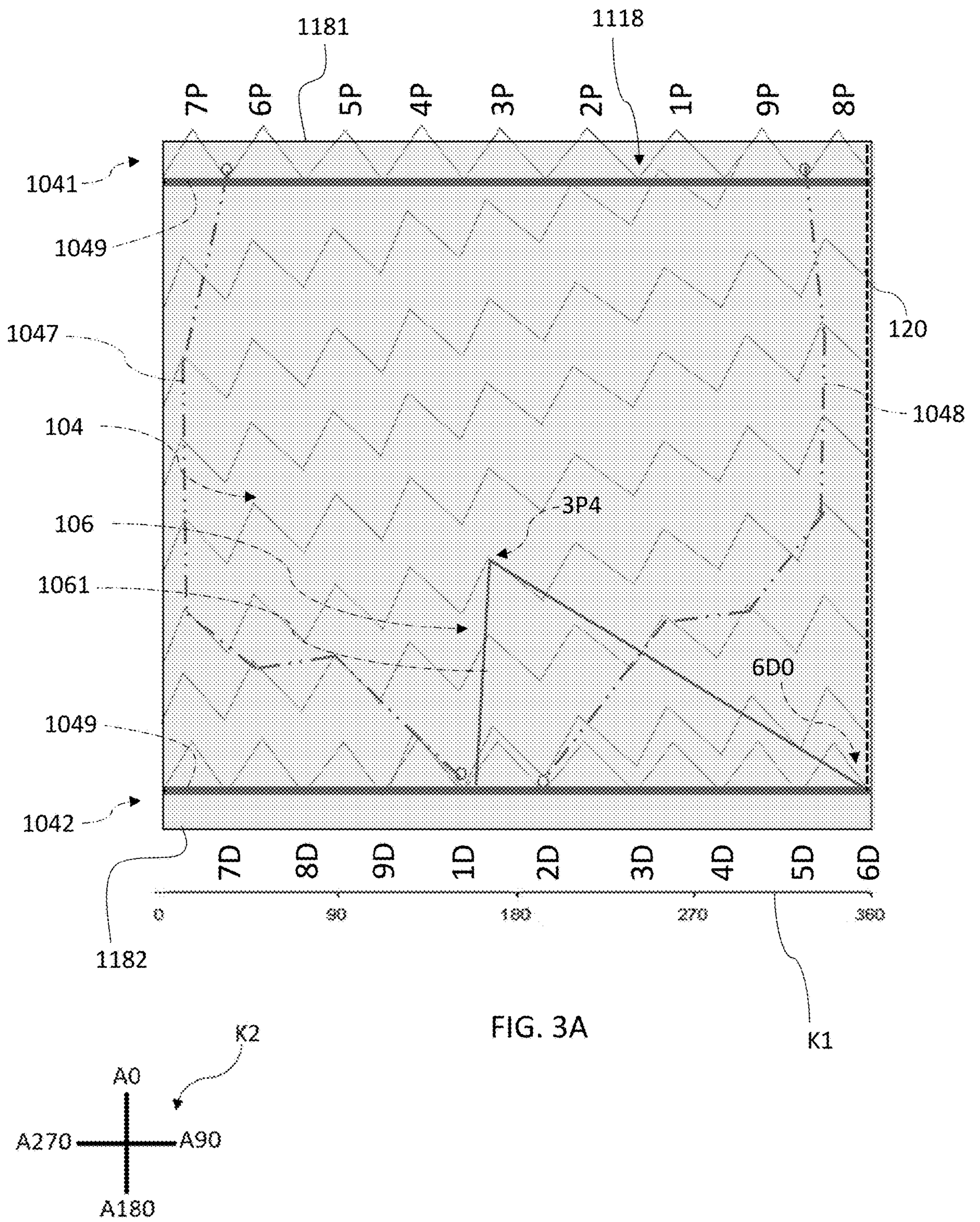
FIG. 3A shows a sleeve with a first deployment line section routing pattern, prior to deployment, according to some embodiments.
Figure 3B:
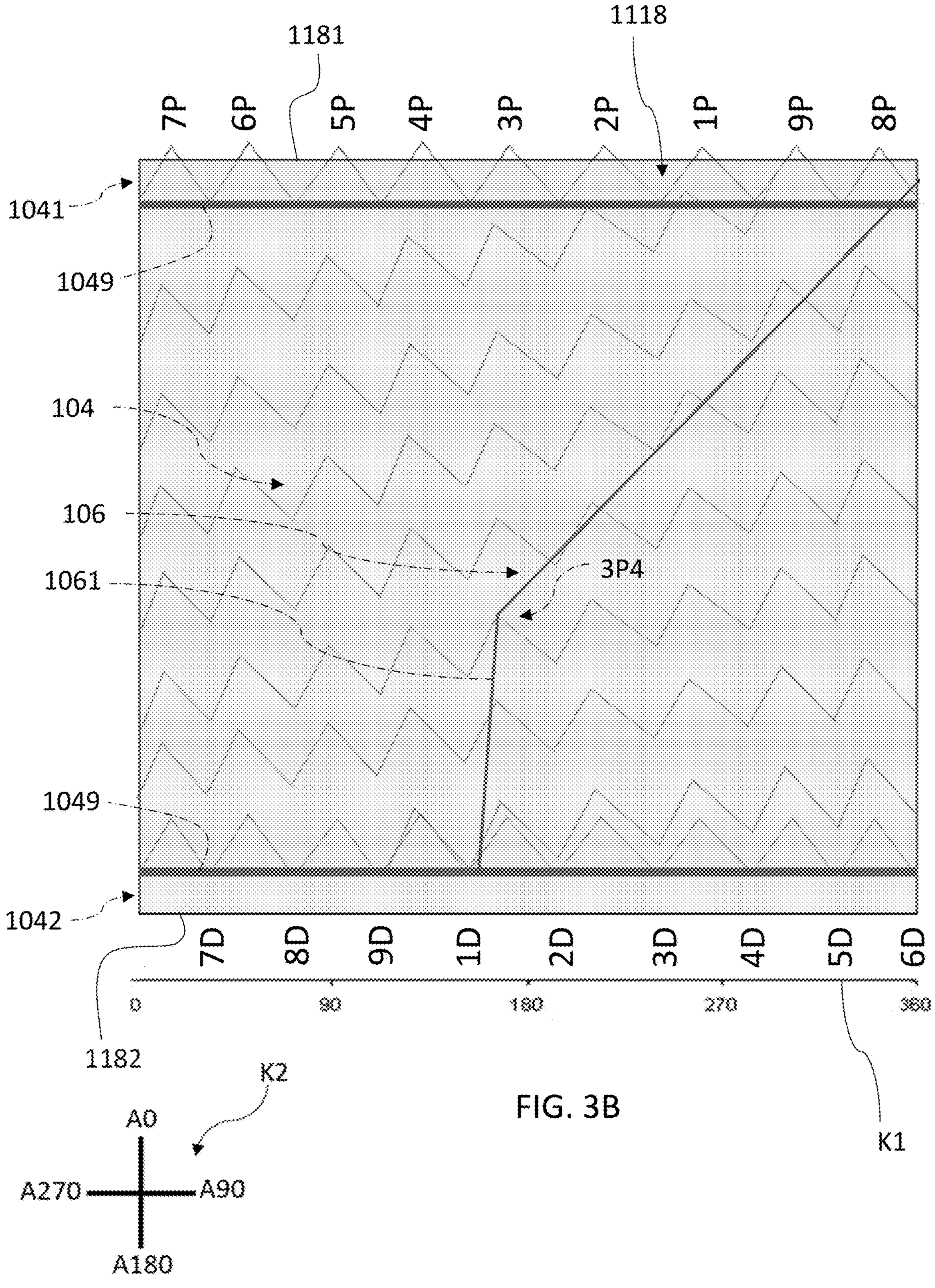
FIG. 3B shows a sleeve with the first deployment line section routing pattern of FIG. 3B, after deployment, according to some embodiments.

Referring now to FIGS. 3A-3B, a plan view of the sleeve 1118 (e.g., delivery sleeve 116 or auxiliary sleeve 118), is shown. As portrayed, the sleeve 1118 is optionally transparent so that underlying features (e.g., the medical device 104) may be viewed beneath the sleeve 1118. In some instances, the medical device 104 may include radiopaque elements 1049 for visibility of the medical device 104 when positioned within a patient. In other instances, the medical device 104 may not include the radiopaque elements. In some instances, the medical device 104 may further include steering lines 1048, 1047 to facilitate bending and steering of the medical device 104 through the vasculature of a patient. In other instances, the medical device 104 may not include the steering lines 1048, 1047. Examples of suitable steering lines and steering line arrangements can be found in U.S. Pat. No. 9,375,308 to Norris, which was issued Jun. 28, 2016 to W. L. Gore & Associates, Inc.

The deployment line 106 defines a primary deployment line, or first deployment line section 1061, and a secondary deployment line, or second deployment line section 1062 (FIG. 4) As shown in FIG. 3A, the first deployment line section 1061 is routed underneath the sleeve 1118 prior to deployment. For example, the first deployment line section 1061 may be routed between the sleeve 1118 and the medical device 104 from near the downstream edge 1182 of the sleeve 1118 to a first anchor point (e.g., a first stent apex) 3P4 positioned proximally of the downstream edge 1182 between the approximately 160° region and the approximately 200° region of the sleeve 1118, routed under the first anchor point 3P4, and then to a starting point of a seam line 120 near a second anchor point 6D0 (e.g., a second stent apex) positioned distally at an angle of between approximately A110° and approximately A160° from the first anchor point 3P4 to begin deployment in the 360° region of the sleeve 1118. As the first deployment line section 1061 is actuated, the sleeve 1118 (e.g., corresponding to delivery sleeve 116 or auxiliary sleeve 118) is deployed along seam line 120 in a proximal direction generally along the 360° region of the sleeve 1118. After deployment of the sleeve 1118 is complete, the first deployment line section 1061 has completed deployment and has changed position, as shown in FIG. 3B.

Upon deployment of the sleeve 1118, at least a portion of the sleeve 1118 may overhang at least a portion of the proximal end 1041 of the medical device 104, which may in turn block or impede the flow of blood in the patient. To ensure efficient and unhindered flow of blood through the patient and the medical device, the overhanging portion of the sleeve may be pulled, peeled, retracted, bunched, pleated, everted, folded, translated, or otherwise moved back from the proximal end 1041 of the medical device 104 as described further herein.

Figure 4A:
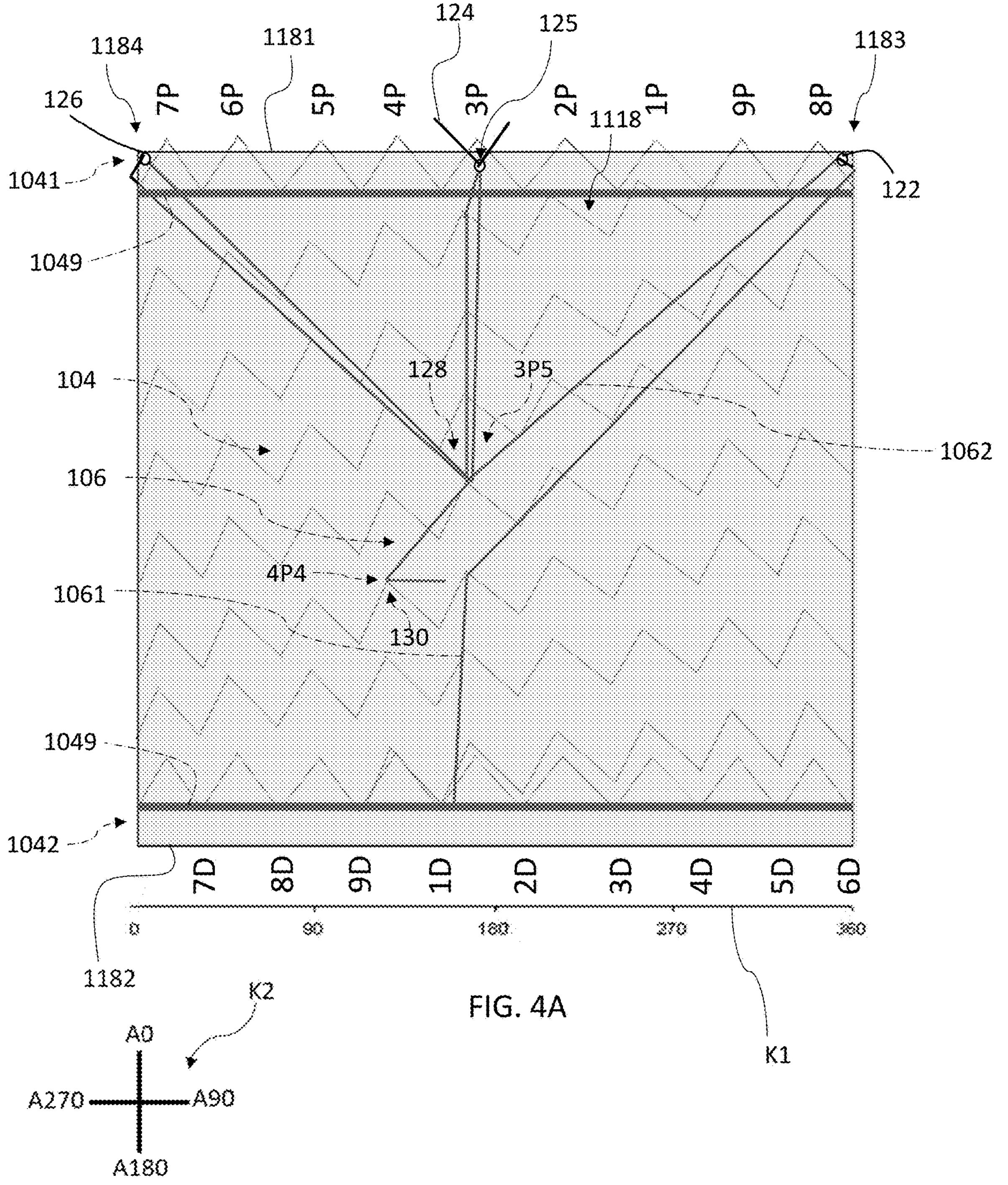
FIG. 4A shows a sleeve with a second deployment line section routing pattern according to some embodiments.

Now referring to FIG. 4A, the sleeve 1118 includes at least a first corner region 1183. In some instances, the sleeve 1118 further includes a second corner region 1184. Each of the first corner region 1183 and the second corner region 1184 become further defined upon deployment. The first corner region 1183 includes an aperture 122, through which the second deployment line section 1062 is routed. The second deployment line section 1062 is then routed under a third anchor point 3P5 (e.g., a third stent apex) positioned proximally at an angle of between approximately A200° and approximately A250° from the first corner region 1183 between the approximately 160° region and the approximately 200° region of the sleeve 1118, which serves as a base point 128. In other instances, multiple base points may be utilized. In any embodiment, the base point 128 may be positioned at any anchor point corresponding with the mid-region 1185 of the sleeve 1118 and may vary depending on the nature of the medical device 104, the diameter of the medical device 104, and other factors.

Figure 4B:
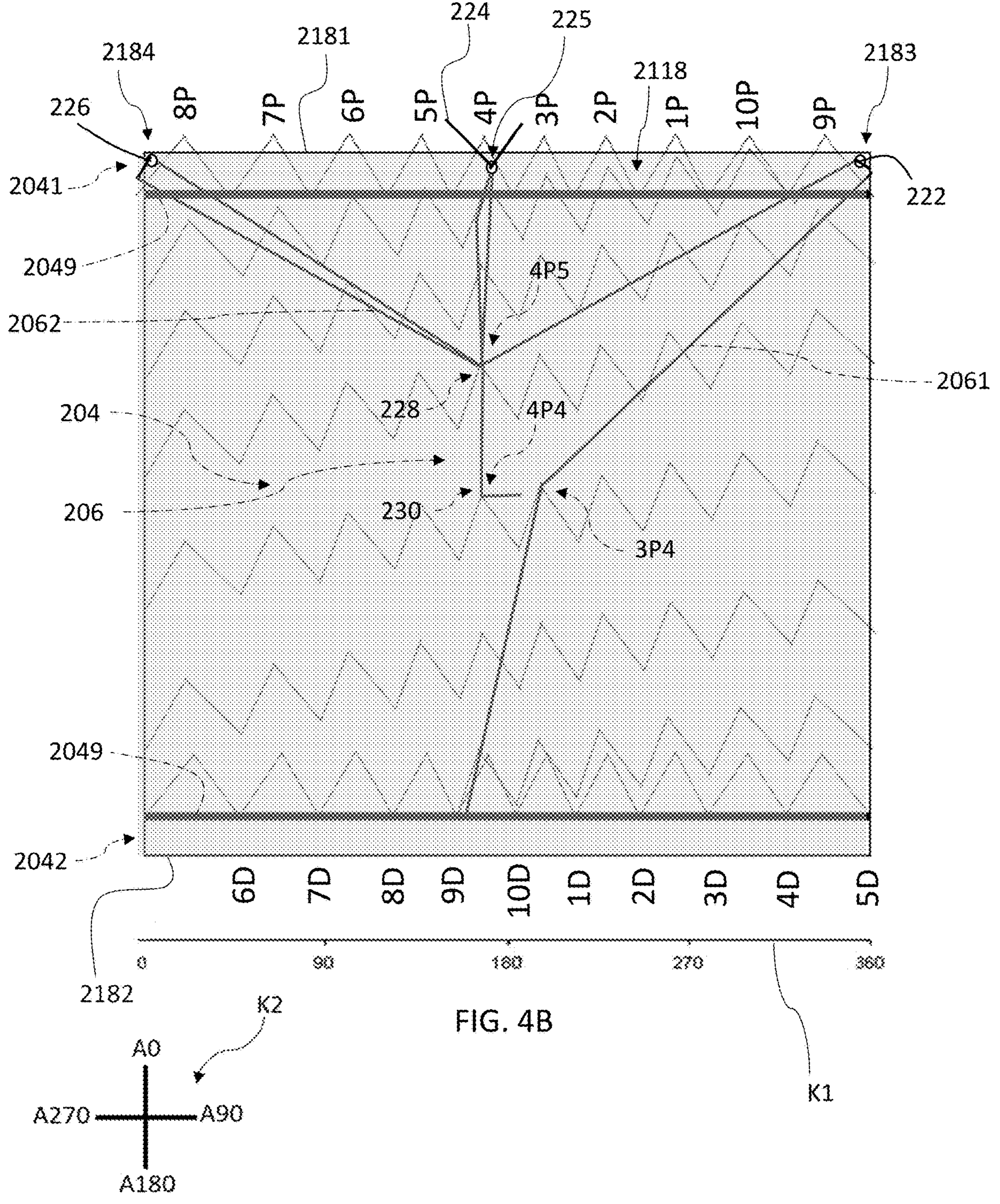
FIG. 4B shows another sleeve with a second deployment line section routing pattern according to some embodiments.

For example, as shown in comparative FIG. 4B, a sleeve 2118 (e.g., corresponding to delivery sleeve 116 or auxiliary sleeve 118) is disclosed. The structure and function of sleeve 2118 is substantially the same to that of sleeve 1118. In some examples, sleeve 2118 has a larger diameter than sleeve 1118, for example. Like elements of the sleeve 2118 are identified by changing the leading "1" to a leading "2" for the corresponding reference number of the sleeve 1118. As shown, a base point 228 may be positioned at a third anchor point 4P5 (e.g., a third stent apex) between the approximately 140° region and the approximately 180° region of the sleeve 2118, while a first deployment line section 2061 may be initially routed under first anchor point 3P4 positioned distally from the third anchor point 4P5 between the approximately 180° region and the approximately 220° region of the sleeve 2118. Other routing changes may be made, while the substantial direction of the routing pattern of the deployment line 106, 206 may be substantially the same.

Referring again to FIG. 4A, after reaching the anchor point 3P5 from the first corner region 1183, the second deployment line section 1062 is routed under the third anchor point 3P5, and then routed up near the upstream edge 1181 of the sleeve 1118, for example, to an aperture 125 near anchor point 3P8, positioned proximally, and generally longitudinally, to the third anchor point 3P5. The second deployment line section 1062 then may attach to a leading attachment fiber 124. For example, in instances including a delivery sleeve 116 (FIG. 2, also described as a primary sleeve) and an auxiliary sleeve 118 (also described as a secondary sleeve), the sleeve 1118 may be either the delivery sleeve 116 or the auxiliary sleeve 118. In one example, where the sleeve 1118 is the auxiliary sleeve 118, the leading attachment fiber 124 may be attached to both the delivery sleeve 116 (FIG. 2) and the auxiliary sleeve 118 to facilitate the attachment of the second deployment line section 1062 to the delivery sleeve 116 (FIG. 2).

In various examples, the second deployment line section 1062 is routed through an aperture 125 located laterally between apertures 122, 126 defining a coupling point with the leading attachment fiber 124 back to the third anchor point 3P5, positioned distally, and generally longitudinally of the coupling point with the leading attachment fiber 124. The second line portion 1062 is again routed, or passed, under the third anchor point 3P5 and is then routed to the second corner region 1184 positioned proximally from the anchor point 3P5 and laterally from the first corner 1183. The second corner region 1184 includes a second aperture 126, through which the second deployment line section 1062 is routed. The second deployment line section 1062 is then routed to back to the third anchor point 3P5 and routed under, passed under, or otherwise slidably anchored to the third anchor point 3P5. The second deployment line section 1062 is routed from the third anchor point 3P5 to a fourth anchor point 4P4 (e.g., a fourth stent apex) positioned distally at an angle of between approximately A200° and approximately A250° from the third anchor point 3P5 between the approximately 110° region and the approximately 160° region of the sleeve 1118, and is further routed under the fourth anchor point 4P4, which acts as a friction point 130 to provide friction to the deployment line 106 to facilitate the actuation of the deployment line 106. The friction point 130 helps prevent the deployment line 106 from slipping out of place, or releasing, before deployment of both the first deployment line section 1061 and the second deployment line section 1062 is complete. In an illustrative embodiment, only one friction point 130 is used, which helps prevent the medical device 104 from slipping while the deployment line 106 is actuated. However, in various instances, multiple friction points 130 may be utilized and be positioned in a variety of places on the medical device 104.

Figure 5A:
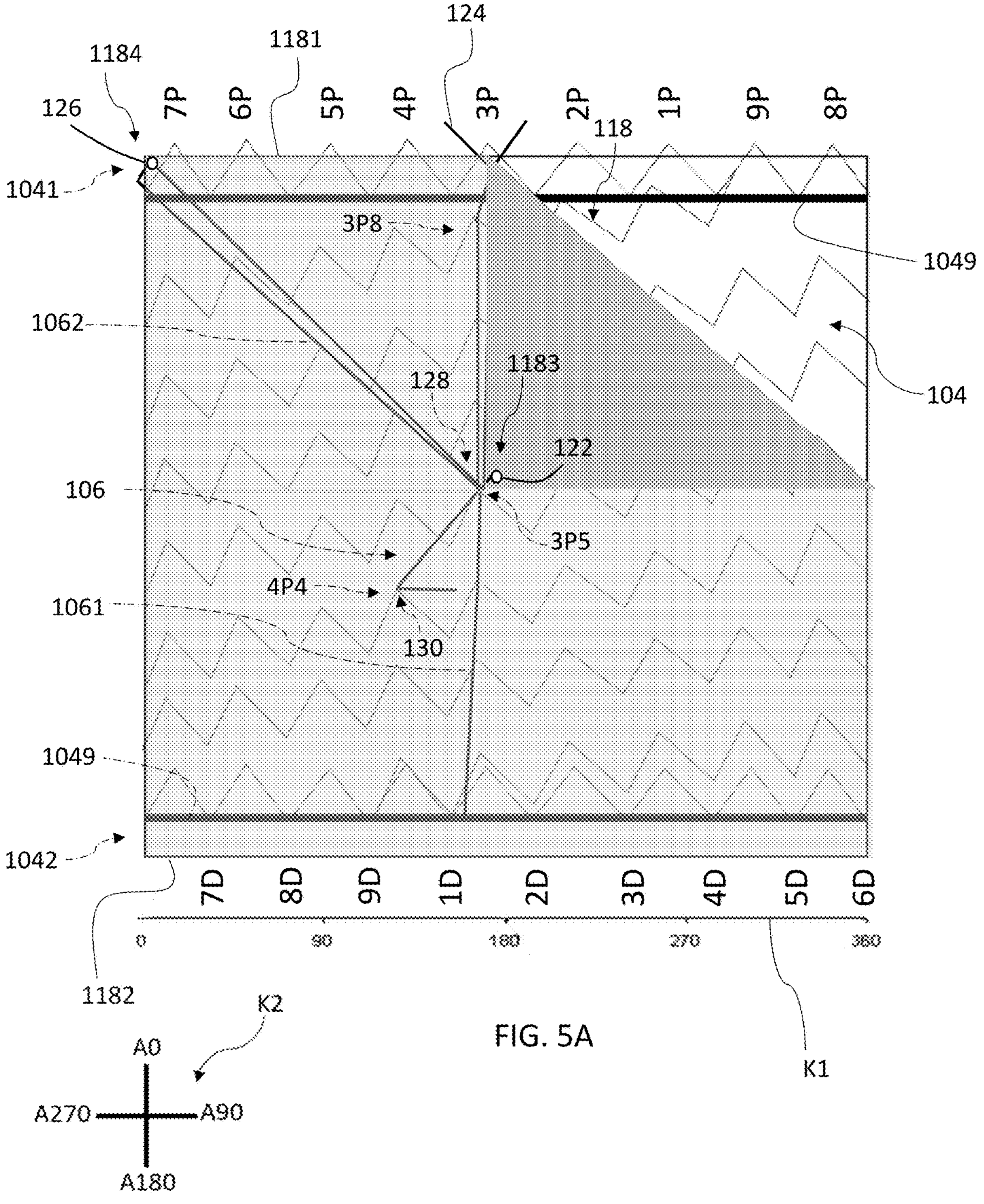
FIG. 5A shows a first configuration of a sleeve during actuation of the second deployment line section of FIG. 4A.
Figure 5B:
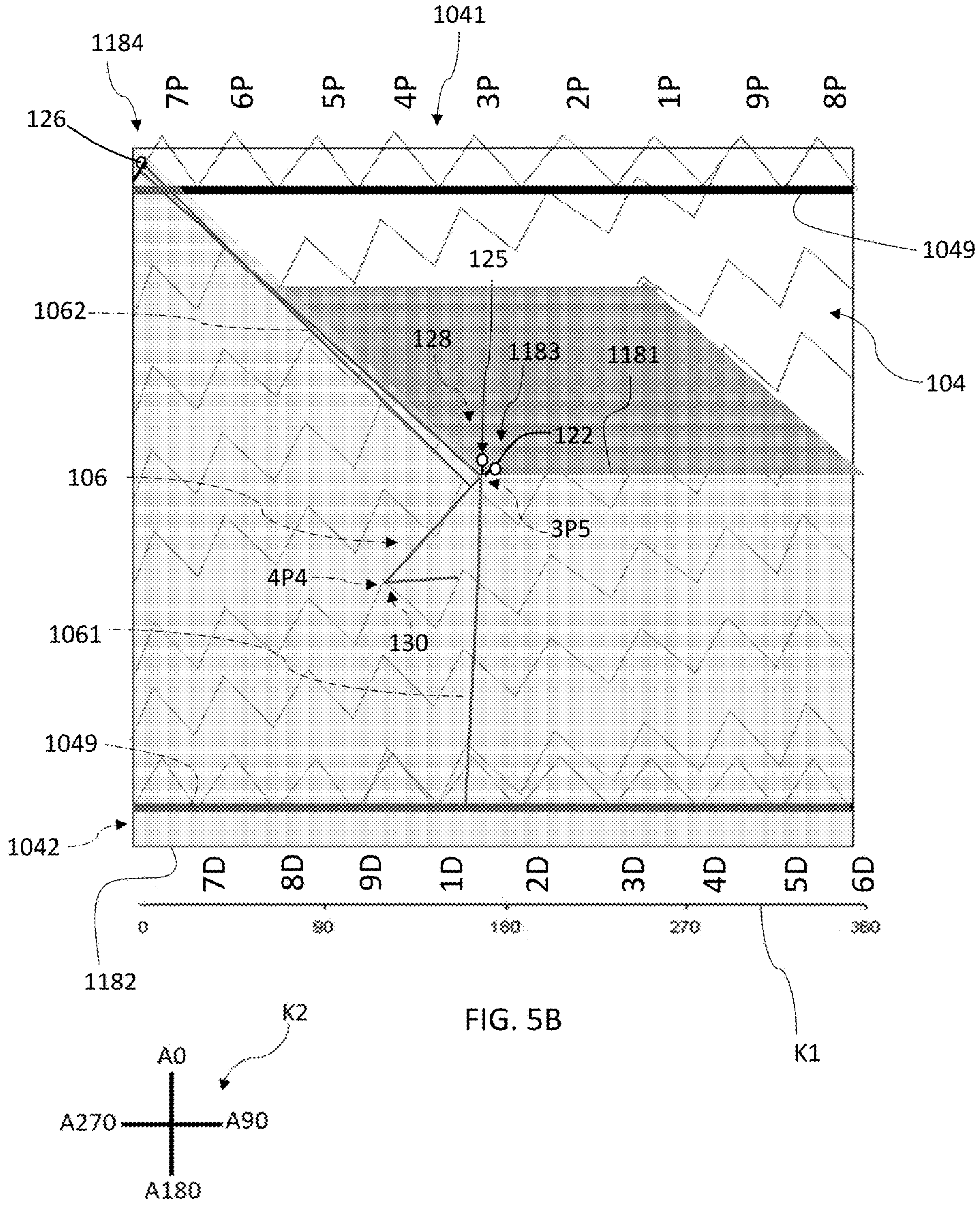
FIG. 5B shows a second configuration of the sleeve of 5A during continued actuation of the second deployment line section.
Figure 5C:
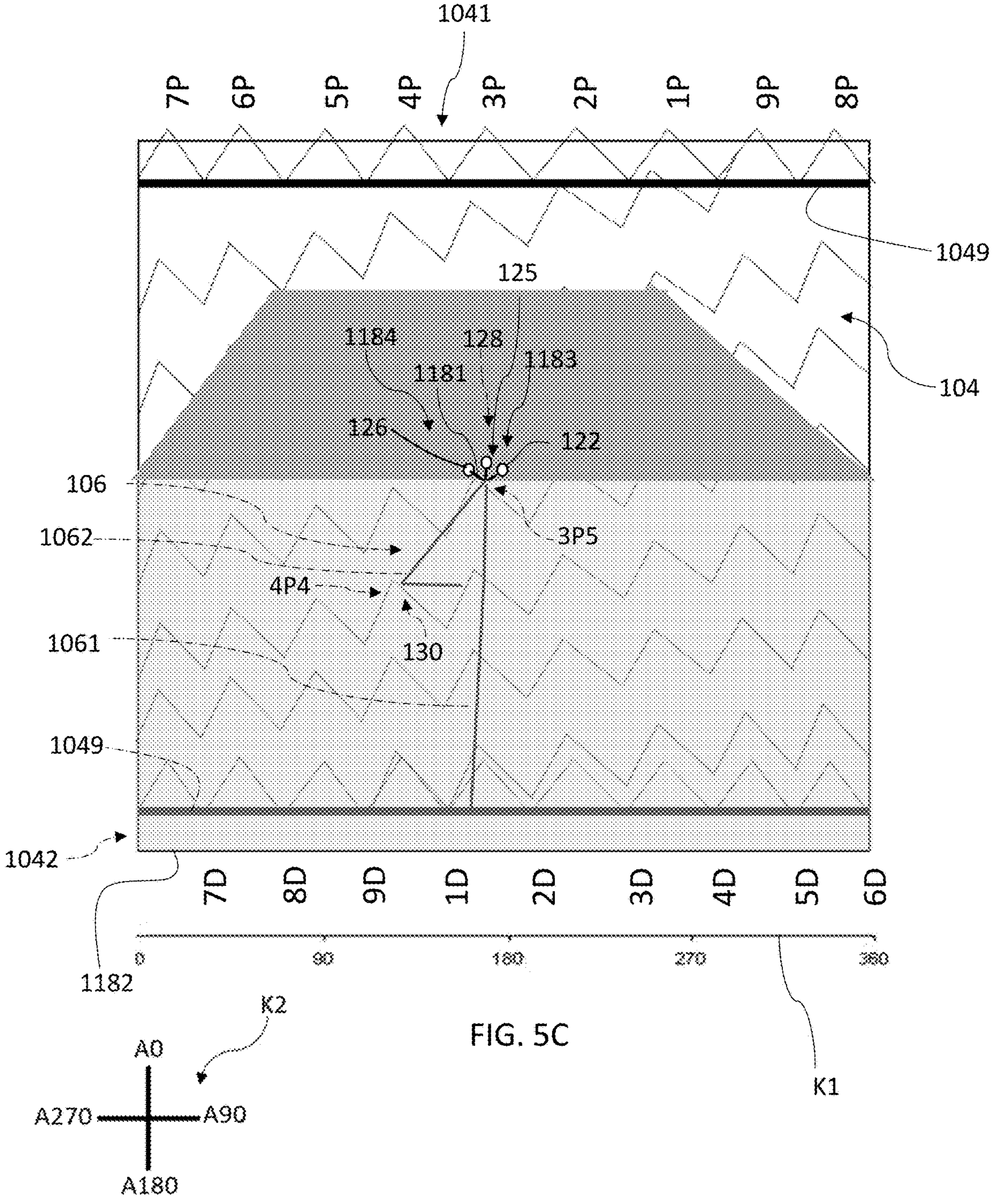
FIG. 5C shows a third configuration of the sleeve of 5B during continued actuation of the second deployment line section.

Referring now to FIGS. 5A-5C, as the deployment line 106 is actuated, after deployment of the first deployment line section 1061 and resultant deployment of the sleeve 1118, the continued actuation of the second deployment line section 1062 results in movement (e.g., pulling, retraction, bunching, pleating, eversion or folding) of the sleeve 1118 according to the routing pattern of the second deployment line section 1062. For example, after deployment of the first deployment line section 1061, as the second deployment line section 1062 is actuated, the first corner region 1183 is pulled, peeled, retracted, bunched, pleated, everted, folded, translated, or otherwise moved back from the proximal edge 1041 of the medical device 104 as shown in FIG. 5A to be gathered toward the base point 128.

As the second deployment line section 1062 continues to be actuated via actuation of the deployment line 106, the upstream, proximal edge 1181 of the sleeve 1118 is pulled, peeled, retracted, bunched, pleated, everted, folded, translated, or otherwise moved back from the proximal edge 1041 of the medical device 104 as shown in FIG. 5B to be gathered at the base point 128. In an embodiment previously described having a delivery sleeve 116 (FIG. 2) and an auxiliary sleeve 118, where the sleeve 1118 is the auxiliary sleeve 118, the delivery sleeve 116 (FIG. 2) may also be pulled, peeled, retracted, bunched, pleated, everted, folded, translated, or otherwise moved back from the proximal edge 1041 of the medical device 104 to be gathered toward the base point 128.

After actuation of the upstream, proximal edge 1181 of the sleeve 1118, as the second deployment line section 1062 continues to be actuated via the deployment line 106, the second corner region 1184 is pulled, peeled, retracted, bunched, pleated, everted, folded, translated, or otherwise moved back from the proximal edge 1041 of the medical device 104 as shown in FIG. 5C to be gathered at the base point 128.

Figure 6:
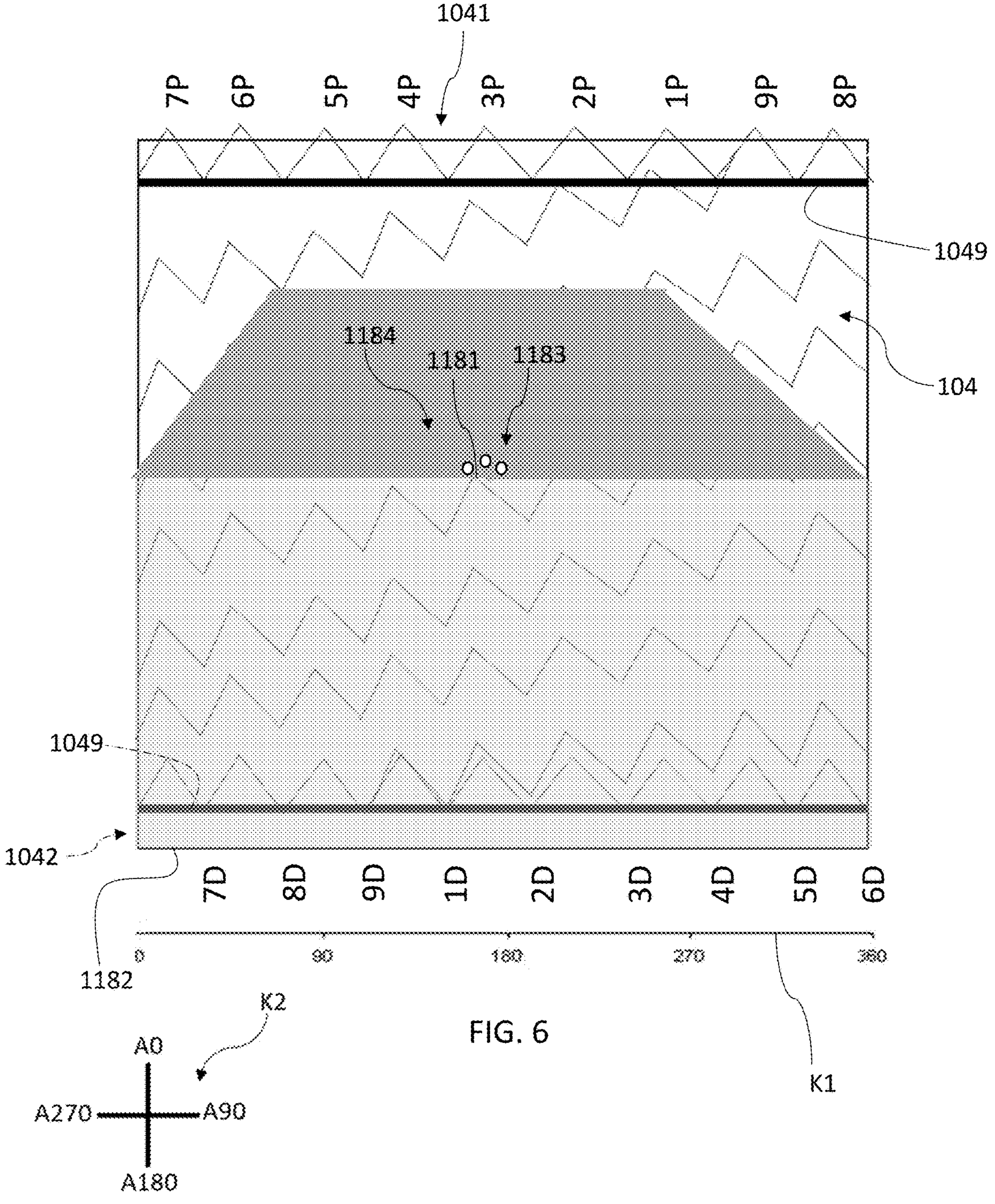
FIG. 6 shows another configuration of a sleeve according to some embodiments after a deployment line has been removed from the sleeve.

As shown in FIG. 6, in some instances, after the corner region(s) 1183, 1184 and the proximal edge 1181 of the sleeve 1118 have been moved back to the base point 128, the user may continue to apply tension to the second deployment line section 1062. As tension is continually applied, the deployment line 106 is released from the sleeve 1118 (and optionally any additional sleeves, such as the delivery sleeve 116), and the anchor point 3P5 or other anchor point located at the base point 128 and is then able to be retracted or pulled out through the catheter 100 (FIG. 1). In other instances, the deployment line 106 may not be released from the sleeve 1118, any other sleeve, and/or the base point 128.

Figure 7A:
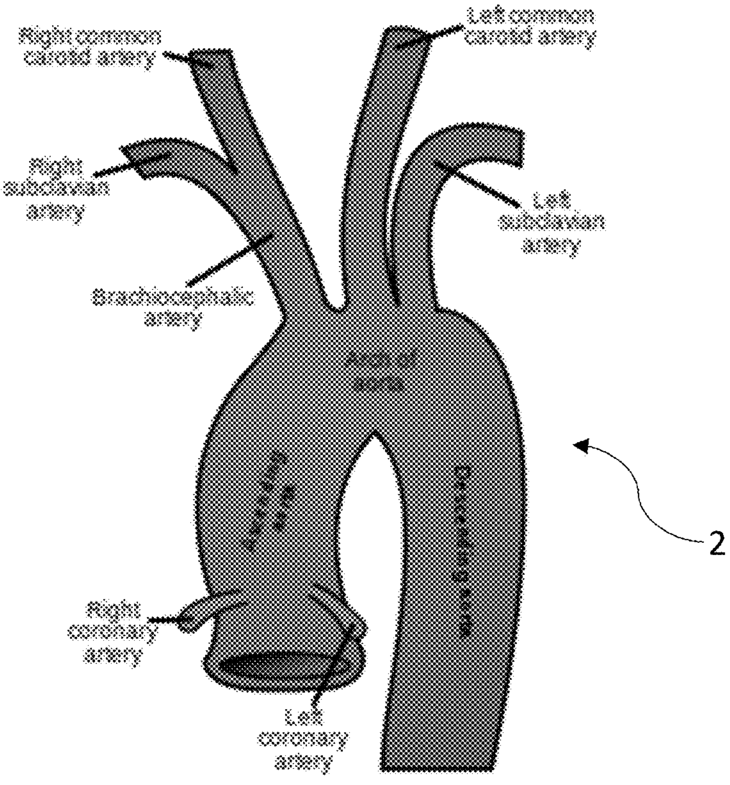
FIG. 7A shows an arch of an aorta of a patient, including an ascending portion of the aorta and a descending portion of the aorta.
Figure 7B:
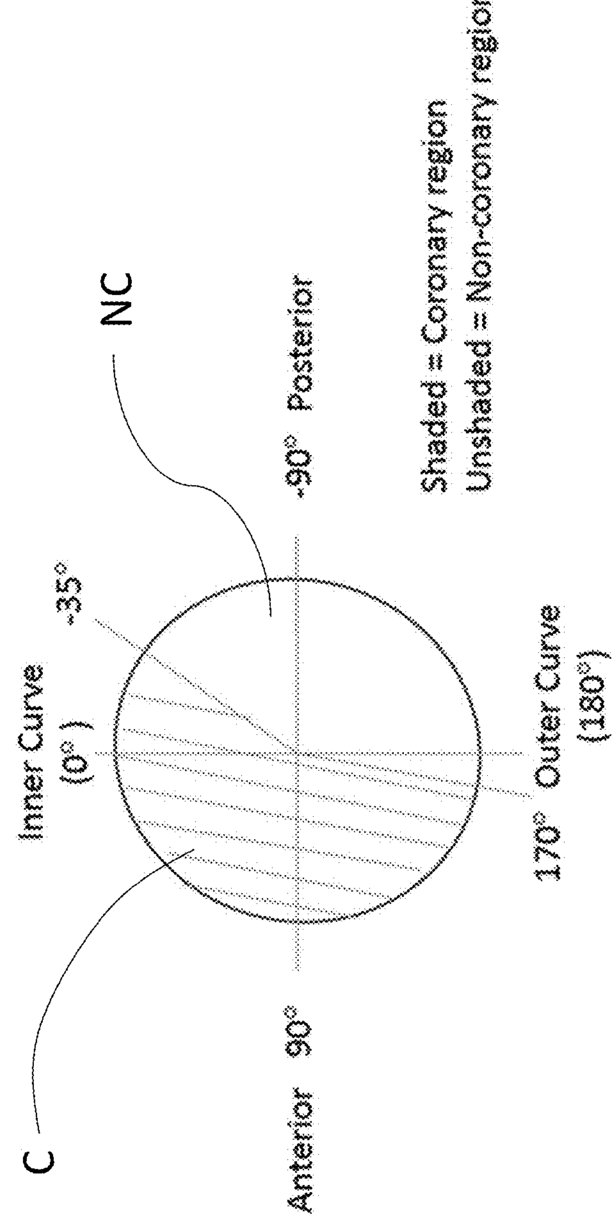
FIG. 7B is a diagrammatic cross-section of an aorta of a patient illustrating the coronary region and the non-coronary region of the aortic cross-section.

In some instances, after full deployment and removal of the deployment line 106, the entirety of the proximal end 1041 of the medical device 104 is unhindered by sleeve overhang as described in detail above. However, in other embodiments, it may be more difficult or nearly impossible to render the entirety of the proximal end 1041 of the medical device 104 unhindered. For example, referring to FIG. 7A, an illustration of an aortic arch 2 is shown, wherein the medical device 104 (FIGS. 1-6) may be deployed. FIG. 7B demonstrates a cross-section of the ascending aorta of FIG. 7A, with the patient's anterior to the left and the patient's posterior to the right. The shaded region C of the cross-section is referred to as the coronary region, while the non-shaded region NC of the cross section is referred to as the non-coronary region. If the medical device 104 (FIGS. 1-6) were to be deployed in the aortic arch 2, at least the coronary region should be unhindered upon full deployment of the medical device 104 (FIGS. 1-6) and actuation of the deployment line 106 (FIGS. 1-6). Thus, in various examples, the medical device 104 and sleeve 1118 are configured such that upon the sleeve 1118 being pulled, retracted, bunched, pleated, everted, folded or otherwise moved away from the end of the medical device 104, preferably an entirety of, but at least the coronary region of the device is unhindered following full deployment of the medical device as described in detail above and with reference to FIGS. 5A-C.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

What is claimed is:

1. A delivery system comprising:

a delivery sleeve releasably secured in a tubular shape configured to constrain a medical device in a delivery configuration, the delivery sleeve having a length, an upstream edge, a downstream edge, a mid-region between the upstream edge and the downstream edge, a first margin extending along the length of the delivery sleeve, a second margin extending along the length of the delivery sleeve, and a first corner region proximate the upstream edge;

a first deployment line section releasably coupling the first and second margins of the delivery sleeve such that the delivery sleeve is releasably secured in a tubular shape; and;

a second deployment line section anchored to the first corner region and routed from the first corner region to a first anchor point at the m id-region, the second deployment line section being configured so that upon actuation of the second deployment line section at least a portion of the upstream edge is translated toward the mid-region.

2. The delivery system of claim 1, wherein the second deployment line section extends from first deployment line section.

3. The delivery system of claim 1, wherein:

the delivery sleeve has a second corner region proximate the upstream edge; and the second deployment line section is anchored to the second corner region and is routed to the first anchor point at the mid-region, the second deployment line section being configured so that upon actuation of the second deployment line section both of the corner regions are translated toward the mid-region.

4. The delivery system of claim 1, wherein the second deployment line section is routed outside of the delivery sleeve.

5. The delivery system of claim 1, wherein the first corner region includes an aperture through which the second deployment line section is routed to anchor the second deployment line section to the first corner region.

6. The delivery system of claim 1, wherein the deployment system includes an auxiliary sleeve.

7. The delivery system of claim 6, wherein the auxiliary sleeve is positioned around the medical device and the delivery sleeve.

8. A delivery system comprising:

a delivery sleeve configured to constrain a medical device in a delivery configuration, the delivery sleeve having a length, an upstream edge, a downstream edge, a mid-region, and a first corner region;

a first deployment line section extending along the length of the delivery sleeve from the downstream edge to the upstream edge to releasably couple the delivery sleeve in a tubular configuration;

a second deployment line section extending from the first deployment line section, the second deployment line section coupled to the first corner region and routed from the first corner region to the mid-region and anchored at the mid-region at a first anchor point.

9. The delivery system of claim 8, wherein the second deployment line section is configured so that upon actuation of the second deployment line section the first corner region is translated back toward the mid-region.

10. The delivery system of claim 8, wherein the first deployment line section and the second deployment line section are releasable from the delivery sleeve.

11. The delivery system of claim 8, wherein:

the delivery sleeve has a second corner region; and the second deployment line section is coupled to the second corner region and is routed from the second corner region to the mid-region and anchored at the first anchor point;

wherein the second deployment line section is configured so that upon actuation of the second deployment line section the first corner region and the second corner region are translated back toward the mid-region.

12. A method for actuating a delivery sleeve of delivery system, the method comprising:

positioning the delivery sleeve at a desired location, the delivery sleeve forming part of a delivery system including, a medical device with which the delivery sleeve is associated, the delivery sleeve having an upstream edge, a downstream edge, a mid-region, and at least one corner; a first deployment line section attached to the delivery sleeve; and a second deployment line section attached to the at least one corner and routed through the mid-region;

applying tension to the first deployment line section such that the first deployment line section actuates the delivery sleeve to effectuate delivery of the medical device; and applying tension to the second deployment line section such that the second deployment line section translates the at least one corner back toward the mid-region.

13. The method of claim 12, wherein the first and second deployment line sections are portions of a single deployment line.

14. The method of claim 12, the method further comprising the step of applying tension to the second deployment line section so that the first deployment line section and the second deployment line section are released from the delivery sleeve.

15. A method for delivering a medical device, the method comprising:

positioning a delivery system at a desired location in a body of a patient, the delivery system including a delivery sleeve associated with a medical device, the delivery sleeve having an upstream edge, a downstream edge, a mid-region, and at least one corner; an auxiliary sleeve positioned around the medical device and the delivery sleeve, the auxiliary sleeve having an upstream edge; a deployment line including a first deployment line section coupled to the first delivery sleeve and a second deployment line section coupled to the auxiliary sleeve, attached to the at least one corner of the delivery sleeve, and routed through the mid-region of the delivery sleeve;

releasing the auxiliary sleeve from about the medical device and the delivery sleeve;

applying tension to the first deployment line section to release the delivery sleeve; and applying tension to the second deployment line section to translate the upstream edges of each of the delivery sleeve and the auxiliary delivery sleeve toward the mid-region of the delivery sleeve.

16. The method of claim 15, wherein the delivery system is coupled to a catheter.

17. The method of claim 16, the method further comprising applying tension to the second deployment line section so that the first deployment line section and the second deployment line section are released from the delivery sleeve and the auxiliary sleeve into the catheter.

18. The delivery system of claim 1, wherein the second deployment line section is directly routed from the first corner region to a first anchor point at the mid-region.

19. The delivery system of claim 1, wherein the first corner region is proximate the first margin or the second margin.

20. The delivery system of claim 1, wherein the first corner region is at the upstream edge.

* * * * *